United States Patent
Bradley et al.

(10) Patent No.: US 6,809,216 B2
(45) Date of Patent: Oct. 26, 2004

(54) FLUORINE-CONTAINING COMPOUNDS AND POLYMERS DERIVED THEREFROM

(75) Inventors: David E. Bradley, Buffalo, NY (US); Jing Ji Ma, West Seneca, NY (US); David Nalewajek, West Seneca, NY (US); George J. Samuels, Williamsville, NY (US); Leonard M. Stachura, Hamburg, NY (US); Michael Van Der Puy, Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 1 day.

(21) Appl. No.: 10/173,916

(22) Filed: Jun. 18, 2002

(65) Prior Publication Data

US 2003/0092828 A1 May 15, 2003

Related U.S. Application Data

(60) Provisional application No. 60/299,083, filed on Jun. 18, 2001.

(51) Int. Cl.$^7$ ............................................. C07C 69/52
(52) U.S. Cl. ....................................................... 560/223
(58) Field of Search ......................................... 560/223

(56) References Cited

U.S. PATENT DOCUMENTS

| | | | |
|---|---|---|---|
| 2,732,370 A | | 1/1956 | Codding .................... 260/91.1 |
| 3,574,791 A | | 4/1971 | Sherman et al. ............ 260/884 |
| 3,654,244 A | | 4/1972 | Pittman et al. ............ 260/79.7 |
| 3,728,151 A | | 4/1973 | Sherman et al. ......... 117/138.8 |
| 3,882,183 A | | 5/1975 | Benninger et al. .......... 260/584 |
| 3,920,614 A | | 11/1975 | Kirimoto et al. ............. 260/63 |
| 3,997,609 A | | 12/1976 | Martini et al. .............. 260/584 |
| 4,125,672 A | * | 11/1978 | Kakuchi et al. ................ 430/5 |
| 4,160,777 A | | 7/1979 | Loudas ........................ 260/456 |
| RE30,337 E | | 7/1980 | Loudas ....................... 252/8.75 |
| 4,433,125 A | * | 2/1984 | Ichinohe et al. ............ 526/279 |
| 4,500,694 A | * | 2/1985 | Ohmori et al. .............. 526/245 |
| 4,559,179 A | | 12/1985 | Hisamoto et al. ........... 260/456 |
| 4,668,726 A | | 5/1987 | Howells ...................... 524/225 |
| 4,681,790 A | | 7/1987 | Fong ............................. 428/96 |
| 4,788,287 A | | 11/1988 | Matsuo et al. ............... 544/196 |
| 4,788,339 A | | 11/1988 | Moore et al. ................ 564/457 |
| 4,792,354 A | | 12/1988 | Matsuo et al. .................. 106/2 |
| 4,795,793 A | | 1/1989 | Amimoto et al. ........... 526/243 |
| 4,859,754 A | | 8/1989 | Mackawa et al. ........... 526/245 |
| 4,859,793 A | * | 8/1989 | Hurtel ......................... 560/223 |
| 4,959,248 A | | 9/1990 | Oxenrider et al. ........ 427/385.5 |
| 5,068,400 A | * | 11/1991 | Tanaka et al. ............... 560/223 |
| 5,274,174 A | | 12/1993 | Shah et al. .................. 560/130 |
| 5,405,677 A | | 4/1995 | Griffith et al. .............. 428/209 |
| 5,562,858 A | | 10/1996 | Bartmann et al. ..... 252/299.66 |
| 5,672,651 A | | 9/1997 | Smith ......................... 524/590 |
| 5,725,789 A | | 3/1998 | Huber et al. ............... 252/8.62 |
| 5,910,557 A | | 6/1999 | Audenaert et al. ........... 528/70 |
| 5,932,760 A | | 8/1999 | Lui et al. .................... 560/223 |
| 5,948,480 A | | 9/1999 | Murphy .................... 427/393.4 |
| 5,998,521 A | | 12/1999 | Fan et al. .................... 524/225 |
| 6,013,732 A | | 1/2000 | Yamana et al. ............. 525/123 |
| 6,019,909 A | | 2/2000 | Ide et al. ....................... 252/70 |
| 6,126,849 A | | 10/2000 | Yamana et al. ............ 252/8.62 |
| 6,133,472 A | | 10/2000 | Nalewajek et al. ......... 560/129 |
| 6,147,268 A | | 11/2000 | Mueller et al. ............. 570/179 |
| 6,177,531 B1 | | 1/2001 | Shimada et al. ............ 526/245 |
| 6,197,378 B1 | | 3/2001 | Clark et al. ................. 427/315 |
| 6,291,704 B1 | | 9/2001 | Anderson et al. ........... 560/227 |
| 2003/0039919 A1 | * | 2/2003 | Bradley et al. .......... 430/270.1 |
| 2003/0109626 A1 | * | 6/2003 | Bradley et al. ............. 524/502 |

FOREIGN PATENT DOCUMENTS

| | | |
|---|---|---|
| JP | 56-53193 | 5/1981 |
| JP | 59-25367 | 2/1984 |
| JP | 60-130669 | 7/1985 |
| JP | 62-103034 | 5/1987 |
| JP | 2-721 | 1/1990 |
| JP | 5-52019 | 3/1993 |
| JP | 7-60096 | 3/1995 |

OTHER PUBLICATIONS

Mason Hayek, Waterproofing and Water/Oil Repellency, 24 Kirk–Othmer Encyclopedia of Chemical Technology 448–65 (3d ed. 1979).

Milos Hudlicky, Chemistry of Organic Fluorine Compounds 2nd Edition, Ellis Horwood Limited, pp 285–288 and 406–410 (1992).

Milos Hudlicky and Attila E. Pavlath, Chemistry of Organic Fluorine Compounds II: A critical Review, ACS Monograph 187, American Chemical Society, p 729–732 (1995).

Nobuo Ishikawa and Akira Nagashima, Bull. Chem. Soc. Japan 49, 502–505 (1976).

Fischer, P. Enol Ethers–Structure and Reactions, in Patai, S., ed. "Chemistry of Ethers, Crown Ethers, Hydroxyl Groups and Their Sulfur Analogues", Wiley, Chichester, UK pp. 761–820 (1980).

Sukhinin et al., Zh. Vses. Khim. O–va., 26(3), 344–345 (1981).

Bayliff, et al., J. Chem. Soc. Perkin Trans. 1,4, 763–767 (1987).

Kanunyants, et al., Ixv. Akad. Nauk SSR Otdel. Khim. Nauk, 282 (1953).

B.M. Monroe and W.K. Smothers, Polymers for Lightwave and Integrated Optics, Technology and Applications, L.A. Hornak, ed., Dekker, p. 145 (1992).

* cited by examiner

Primary Examiner—D. R. Wilson
(74) Attorney, Agent, or Firm—Deborah M. Chess

(57) ABSTRACT

Provided are fluorine-containing compounds, and polymers derived therefrom, for use in compositions used for treating textile substrates. The present invention further provides methods of making fluorine-containing compounds and polymers derived therefrom, compositions comprising the compounds and/or polymers of the present invention, methods of treating substrates, and the treated products derived therefrom.

3 Claims, No Drawings

FLUORINE-CONTAINING COMPOUNDS AND POLYMERS DERIVED THEREFROM

CROSS-REFERENCE TO RELATED APPLICATION

This application claims priority to U.S. Provisional Application Ser. No. 60/299,083, which was filed with the United States Patent and Trademark Office on Jun. 18, 2001, and is incorporated herein by reference.

FIELD OF INVENTION

The present invention relates generally to fluorine-containing compounds, and polymers derived therefrom, for use in compositions used for treating textile substrates. The present invention further relates to methods of making fluorine-containing compounds and polymers derived therefrom, compositions comprising the compounds and/or polymers of the present invention, methods of treating substrates, and the treated products derived therefrom.

BACKGROUND

Fluorine-containing compounds have found use in a wide range of industrial applications including, for example, textile coating applications. Because such fluorine-containing compounds, and the polymers derived therefrom, form coatings which tend to increase the water repellency, oil repellency, and/or soil resistance of substrates, they are desirable for use in treating and protecting the surfaces of such substrates.

Unfortunately, such known fluorochemicals tend to be environmentally undesirable. Many of such known chemicals tend to biodegrade, at least in part, to form compounds such as perfluorocarboxylic acids. Perfluorocarboxylic acids have long and potentially damaging lifetimes in environment. Also, such compounds are not readily metabolized in the human body and tend to bioaccumulate in the liver. Thus, ingestion or inhalation of such compounds can be detrimental to human health.

Recognizing these and other drawbacks of the related art, the present inventors have perceived a need for new fluorine-containing compounds which are not only suitable for use in a variety of applications, especially textile coatings applications, but also are environmentally desirable and have relatively low toxicity. These and other objects are achieved by the present invention as described below.

SUMMARY OF THE INVENTION

The present invention is directed to a family of fluorine-containing compounds, and polymers derived therefrom, for use in the preparation of compositions used in various coatings or textile-treatment applications. The compounds of the present invention are advantageous over fluorinated compounds used conventionally to treat textiles in that the present compositions tend to biodegrade more readily, and, upon biodegradation, tend to form compounds that are more environmentally-desirable and less toxic than conventional compounds.

Accordingly, one aspect of the present invention relates to fluorine-containing compounds. In preferred embodiments, the present invention provides fluorine-containing compounds which are described by the following formula:

$$CH_2=C(R^1)C(O)O-(Y-O)_a-CR^2R^3-CF_2CHFCF_3 \qquad (1)$$

wherein: $R^1$, $R^2$ and $R^3$ are independently hydrogen or lower alkyl, Y is a divalent organic moiety, and a is zero or one.

Another aspect of the present invention is a family of polymers comprising at least one repeating unit derived from the compounds of the invention. In preferred embodiments, the polymers of the present invention comprise at least one repeating unit derived from a compound of formula (1).

The compounds and polymers of the present invention are useful compositions designed to impart water repellency to a substrate. Therefore, yet another aspect of the present invention is a composition comprising a polymer of the present invention.

Yet another aspect of the present invention relates to a method for treating a substrate with a composition of the present invention comprising applying a layer of the composition of the invention onto a substrate and curing the composition on the substrate.

The inventive method produces articles of manufacture having water and soil-repellent coatings. Therefore, still another aspect of the present invention is a substrate having a water-resistant and/or soil-resistant coating produced via the method of the present invention.

The compositions comprising polymers or compounds of the present invention may be cured to form films. Therefore, another aspect of the present invention includes the films produced by curing the compositions of the present invention.

DESCRIPTION OF THE PREFERRED EMBODIMENTS

Monomer Compounds

In certain embodiments, the present invention provides fluorine-containing compounds which are described by the formula as follows:

$$CH_2=C(R^1)C(O)O-(Y-O)_a-CR^2R^3-CF_2CHFCF_3 \qquad (1)$$

wherein: $R^1$, $R^2$ and $R^3$ are independently hydrogen or lower alkyl, Y is a divalent organic moiety, and a is zero or one.

As used herein, the term "lower alkyl" is a substituted or unsubstituted alkyl group having from about 1 to about 6 carbon atoms. Examples of lower alkyl groups are methyl, ethyl, n-propyl, isopropyl, butyl, sec-butyl, tert-butyl, n-pentyl, isopentyl, neopentyl, and n-hexyl. Lower alkyl groups may be further substituted with other substituents including, for example, halogens, alkoxy, alkyl, fluoroalkyl groups, and the like. Certain preferred lower alkyls include unsubstituted alkyls having from about 1 to about 3 carbons, such as, methyl, ethyl, n-propyl, and isopropyl.

In the compounds of the present invention, Y is a divalent organic moiety comprising a carbon atom available for bonding to a C(O)—O— group and a carbon atom available for bonding to an —OCR²R³—CF₂CHFCF₃ group, wherein the carbon atom(s) available for bonding to the C(O)—O— and —OCR²R³—CF₂CHFCF₃ groups may be the same carbon atom or different carbon atoms. Y as a divalent organic moiety may be any suitable divalent substituted or unsubstituted aliphatic or aromatic moiety.

Suitable divalent substituted or unsubstituted aliphatic or aromatic moieties include those derived from monovalent aliphatic or aromatic groups. As will be recognized by those of skill in the art, divalent radicals can be derived from a wide variety of monovalent aliphatic or aromatic groups by removing one hydrogen from a carbon atom of the monovalent group. For example, suitable divalent aliphatic moieties for use in the present invention include those derived from alkyls, alkenyls, alkynyls, cycloalkyls, cycloalkenyls, cycloalkynyls, heteroalkyls, heteroalkenyls, heteroalkynyls, aryls, aralkyls, and combinations of two or more thereof.

Y as an divalent aliphatic moiety can be derived, as indicated above, from any of a wide range of alkyl groups. Preferably, Y is derived from an alkyl group having from about 1 to about 20 carbon atoms. The $C_1$–$C_{20}$ alkyl group may be a straight chain or branched molecule, for example: methyl, ethyl, n-propyl, isopropyl, n-butyl, isobutyl, tert-butyl, n-pentyl, neopentyl, n-hexyl, n-heptyl, n-octyl, 2-ethylhexyl, nonyl, decyl, and the like. Additionally, any of the alkyl groups, from which Y is derived, may be further substituted with other substituents including alkoxy and aryloxy groups, such as —O—$CR^2R^3$—$CF_2CHFCF_3$ groups wherein each $R^2$ and $R^3$ in the compound of Formula 1 is independently selected, as well as, halogen, alkyl, fluoroalkyl, arylalkyl groups, and the like. (As used herein, the term "independently selected" means that each Z group in a given compound of Formula 1 can be the same or different from any one or more Z groups present in the compound.) In a preferred class of divalent moieties, Y is derived from a substituted or unsubstituted $C_2$–$C_6$ alkyl, and more preferably a substituted or unsubstituted $C_2$–$C_4$ alkyl. Examples of such more preferred Y moieties include: —$CH_2CH_2$—, —$CH(CH_3)CH_2$—, —CH(O—$CR^2R^3$—$CF_2CHFCF_3$)—, and the like.

Y as an divalent aliphatic moiety can be derived from any of a wide range of alkenyl groups. Preferably, Y is derived from an alkenyl group having from about 2 to about 20 carbon atoms. The $C_2$–$C_{20}$ alkenyl may be a straight chain or branched molecule, for example, ethenyl, propenyl, butenyl, penentyl, hexenyl, heptenyl, octenyl, 2-ethylhexenyl, nonenyl, decenyl, and the like. Additionally, any of the alkenyl groups, from which Y is derived, may be further substituted with other substituents including alkoxy and aryloxy groups, such as —O—$CR^2R^3$—$CF_2CHFCF_3$, as well as, halogen, alkyl, fluoroalkyl, arylalkyl groups, and the like.

Y as an divalent aliphatic moiety can be derived from any of a wide range of alkynyl groups. Preferably, Y is derived from an alkynyl group having from about 2 to about 20 carbon atoms. The $C_2$–$C_{20}$ alkynyl may be a straight chain or branched molecule, for example, ethynyl, propynyl, butynyl, penyntyl, hexynyl, heptynyl, octynyl, 2-ethylhexynyl, nonynyl, decynyl, and the like. Additionally, any of the alkynyl groups, from which Y is derived, may be further substituted with other substituents including alkoxy and aryloxy groups, such as —O—$CR^2R^3$—$CF_2CHFCF_3$, as well as, halogen, alkyl, fluoroalkyl, arylalkyl groups, and the like.

Y as an divalent aliphatic moiety derived from a cycloalkyl group is preferably derived from a cycloalkyl having from about 3 to about 20 carbon atoms. Examples of suitable $C_3$–$C_{20}$ cycloalkyls include, for example, cyclopentyl, cyclohexyl, cycloheptyl, cyclooctyl, cyclononyl, cyclodecyl, and the like. Additionally, any of the cycloalkyl groups, from which Y is derived, may be further substituted with other substituents including alkoxy and aryloxy groups, such as —O—$CR^2R^3$—$CF_2CHFCF_3$, as well as, halogen, alkyl, fluoroalkyl, arylalkyl groups, and the like.

Y as an divalent aliphatic moiety derived from a cycloalkenyl group is preferably derived from a cycloalkenyl having from about 5 to about 20 carbon atoms. Examples of suitable $C_5$–$C_{20}$ cycloalkenyls include, for example, cyclopentenyl, cyclohexenyl, cycloheptenyl, cyclooctenyl, cyclononenyl, cyclodecenyl, and the like. Additionally, any of the cycloalkenyl groups, from which Y is derived, may be further substituted with other substituents including alkoxy and aryloxy groups, such as —O—$CR^2R^3$—$CF_2CHFCF_3$, as well as, halogen, alkyl, fluoroalkyl, arylalkyl groups, and the like.

Y as an divalent aliphatic moiety derived from a cycloalkynyl group is preferably derived from a cycloalkynyl having from about 5 to about 20 carbon atoms. Examples of suitable $C_5$–$C_{20}$ cycloalkynyls include, for example, cyclopentynyl, cyclohexynyl, cycloheptynyl, cyclooctynyl, cyclononynyl, cyclodecynyl, and the like. Additionally, any of the cycloalkynyl groups, from which Y is derived, may be further substituted with other substituents including alkoxy and aryloxy groups, such as —O—$CR^2R^3$—$CF_2CHFCF_3$, as well as, halogen, alkyl, fluoroalkyl, arylalkyl groups, and the like.

Y as derived from a heteroalkyl, heteroalkenyl, or heteroalkynyl preferably comprises a divalent moiety derived from an open-chain or cyclic, alkyl, alkenyl, or alkynyl group, as described above, further including at least one heteroatom, such as, nitrogen (N) and/or sulfur(S).

Y as a divalent aromatic moiety derived from an aryl group is preferably derived from an aryl comprising from about 5 to about 20 carbon atoms. The $C_5$–$C_{20}$ aryl may be, for example, phenyl, o-tolyl, m-tolyl, p-tolyl, o-xylyl, m-xylyl, p-xylyl, alpha-naphthyl, beta naphthyl and the like. Additionally, any of the aryl groups, from which Y is derived, may be further substituted with other substituents including alkoxy and aryloxy groups, such as —O—$CR^2R^3$—$CF_2CFCF_3$, as well as, halogen, alkyl, fluoroalkyl, arylalkyl groups, and the like.

Y as derived from an aralkyl is preferably derived from an aralkyl having from about 6 to about 20 carbon atoms. The $C_6$–$C_{20}$ aralkyl may be, for example, benzyl, 4-methylbenzyl, o-methylbenzyl, p-methylbenzyl, diphenylmethyl, 2-phenylethyl, 2-phenylpropyl, 3-phenylpropyl and the like. Additionally, any of the aralkyl groups, from which Y is derived, may be further substituted with other substituents including alkoxy and aryloxy groups, such as —O—$CR^2R^3$—$CF_2CHFCF_3$, as well as, halogen, alkyl, fluoroalkyl, arylalkyl groups, and the like.

By way of further illustration, the following is a list of compounds from which can be derived further examples of divalent aliphatic and aromatic Y groups suitable for use in the present invention. In general, it is to be understood that suitable Y groups may be derived from the compounds listed below, for example, by removing a hydrogen or hydroxyl group from a carbon atom (to form a carbon atom for bonding to C(O)—O— group), and removing a hydrogen or hydroxyl group from a carbon atom (which can be the same or different carbon atom for bonding to the C(O)—O— group) to form a carbon atom for bonding to a —O—$CR^2R^3$—$CF_2CHFCF_3$ group. The compounds include:

aliphatic alcohols, such as, 1,3-propanediol, 1,2-propanediol, n-butanol, sec-butanol, isobutanol, tert-butanol, dihydroxy butanes,1,4-butanediol, 1,3-butanediol, 1,2-butanediol, 2-methyl-1-3-propanediol, neopentylglycol, 2-pentene 1,5-diol, 2-pentene 1,4-diol, 2-pentene 4,5-diol, 1-pentene-3,4-diol, 1-pentene-4,5-diol, 1-pentene-3,5-diol, 2-butene 1,4-diol, 1-butene-3,4,-diol, 2-butyne 1,4-diol, 1-butyne-3,4-diol, pentane 1,5-diol, pentane 1,4-diol, pentane 1,3-diol, pentane 1,2-diol, pentane 2,5-diol, pentane 2,4-diol, pentane 2,3-diol, 2-methyl-1,1,2,3-propanedtriol, pentane-1,2,3-triol, pentane-1,2,4-triol, pentane-1,2,5-triol, pentane-1,3,5-triol, pentane-1,3,4-triol, pentane-2,3,4-triol, 2-ethyl 1,2,3,-propanetriol, butane 1,2,3,4 tetraol, pentaeryheixtol, pentane 1,2,3,4 tetraol, pentane 1,2,3,5 tetraol, pentane 1,2,4,5 tetraol, 2-methylene-propane-1,3-diol, 2-ethylidne-propane-1,2-diol, 1-isopropyidene-propane-1,3-diol, 2,3-dimethyl-but-2-ene-1,4-diol, 2-ethyl-but-2-ene-1,4-diol, and 2-methyl-but-2-ene-1,4-diol, 2-Hydroxymethyl-2-methyl-propane-1,3-diol, 2-Hydroxymethyl-propane-1,3-diol, 2-Ethyl-2-hydroxymethyl-propane-1,3-diol, 2-Hydroxymethyl-propane-1,2,3-triol, 2-Hydroxymethyl-butane-1,2,3-triol, 2-Hydroxymethyl-butane-1,2,4-triol, 3-Hydroxymethyl-butane-1,2,4-triol, 1,2,3 trihydroxy propane, pentaerythritol, di-pentaerytheritol, tripentaerythritol, glycerol propoxylate, meso-erythritol, $HOCH_2[CH(OH)]_2CH_2OH$, threitol DL, 1,2,3,4 butanetetrol, sorbitol, $HOCH_2[CH(OH)]_4CH_2OH$, mannitol, $HOCH_2[CH(OH)]_4CH_2OH$, dulcitol, iditol, L-sorbose, $HOCH_2(HCOH)_3C(O)CH_2OH$, 1,1,1 tris(hydroxymethyl)ethane, 1,2,3 trihydroxy hexane, 1,2,6 trihydroxy hexane, trimethylol propane $CH_3CH_2(CH_2OH)_3$, trimethylol propane ethoxylate $CH_3CH_2(CH_2O(CH_2CH_2O)_xCH_2CH_2OH)_3$, trimethylol propane propoxylate $CH_3CH_2(CH_2O(CH_3CHCH_2O)_xCH_3CHCH_2OH)_3$, trimethylol propane allyl ether, 1,4 dihydroxy-2-butene $HOCH_2CH=CHCH_2OH$, 1,4 dihydroxy-2-butyne $HOCH_2CCCH_2OH$, 3-methyl-3-oxetanemethanol $CH_3C(CH_2OH)CH_2OCH_2$, 3-ethyl-3-oxetanemethanol $CH_3CH_2C(CH_2OH)CH_2OCH_2$, N, N, bis(hydroxyethyl)acryl-amide, N, N, bis(2-hydroxypropyll)acrylamide, cyclic polyols, such as, 1,2-cyclopentonediol, 1,2-cyclohexanedimethanol, 1,3-cyclopentanediol, 1,4-cyclohexandimethanol, 1,2-cyclopentanediol, 1,3-cyclohexandimethanol, 1,2-cyclohexanediol, 1-4-cyclohexandeiol, 1,3,5-cyclohexanetriol, triethanol amine, tetrahydroxyethyl ethylene diamine, 3-amino-1,2-propanediol, 2-amino-2-methyl-1,3-propanediol $(HOCH_2)_2CCH_3NH_2$, tris(hydroxymethyl)aminomethane $(HOCH_2)_3CNH_2$, tris(hydroxymethyl)aminomethylacrylamide $(HOCH_2)_3CNHC(O)CH=CH_2$, methyolacrylamide $(HOCH_2NHC(O)CH=CH_2)$, dihydroxyethylacrylamide $(HOCH_2CH_2)_2NC(O)CH=CH_2)$, dihydroxymethylacrylamide $((HOCH_2)_2NC(O)CH=CH_2)$, and the methyl substituted acrylamides;

aryl alcohols, such as, benzene 1,2 diol; benzene 1,2,3,4 tetraol; benzene 1,3 diol; benzene 1,2,3,5 tetraol; benzene 1,4 diol; benzene 1,2,4,5 tetraol; benzene 1,2,4 triol; bis phenol A; benzene 1,3,4-triol; bis phenol AF; benzene 1,2,3-triol; 4, hexafluoroacetone(6FK) phenol; 1,3 bis 6FK benzene; 1,4 bis 6FK benzene; 2-hydroxybenzylalcohol; 3-hydroxybenzylalcohol; 4-hydroxybenzylalcohol; phenylene 1,3-diamine; 1,2-benzene dimethanol; phenylene 1,3-diamine; 1,3-benzene dimethanol; phenylene 1,4-diamine; 1,4-benzene dimethanol; 1,2,3-benzenetrimethanol; 1,2,4,5-benzenetetramethane; 1,2,4-benzenetrimethanol; 1,2,3,4-benzenetetramethane; 1,3,5-benzenetrimethanol; 1,2,3,4-benzenetetramethane, aniline, phenol sulfonic acid;

polymers and copolymers with alcohol functional groups, for example, multiple co-polymers can be prepared with monomers that contain "free" hydroxyl groups such as hydroxethyl(meth)acrylate, hydroxpropyll(meth)acrylate, allyl alcohol, and hydroxy vinyl ethers such as hydroxyethyl vinyl ether and hydroxybutyl vinyl ether, for example, poly(2-hydroxyethylacrylate), poly(2-hydroxyethylmethacrylate), poly(2-hydroxypropylacrylate), poly(4-hydroxystyrene), poly(hydroxyethyl vinyl ether), poly(hydroxybutyl vinyl ether), poly(styrene-co-allyl alcohol), polyvinyl alcohols, poly(vinyl alcohol-co-ethylene), poly(vinylchloride-co-vinylacetate-co-2-hydroxypropyl acrylate), poly(vinyl phenol-co-methyl methacrylate), poly(vinyl phenol-co-2-hydroxyethyl methacrylate), poly(vinyl pyridine-co-2-hydroxymethylacrylate);

saccharides, which as used herein means a saccharide residue wherein a hydrogen atom is removed from the hydroxyl group attached to the anomeric carbon atom of the saccharide and is replaced with a polymerizable moiety; the remaining hydroxyl groups are partially or completely replaced by fluoroethers; more specifically they are the saccharide residues of monosaccharide or oligosaccharide having about 1 to about 10, preferably about 1 to about 5, more preferably about 1 to 3, sugar units; and their respective glycans, for example, methylglueth-10, or other ethylene oxide or propylene oxide adducts of the saccharide;

water soluble gums, including Guar, Gum Arabic, Karaya, Tragacanthin, Xanthan;

vinyl ethers including, ethylvinylether, trimethylolpropane vinyl ether, butylvinyl ether, trimethylol propane divinyl ether, cyclohexylmethyl vinyl ether, pentaetherital vinylether, glycerolmono vinyl ether, pentaetherital divinyl ether, glycerol divinyl ether, pentaetheriotal trivinyl ether, dioxole;

furfuryl alcohol, bis-hydroxy-methyl furan, linear or branched ketene acetals of the formula $C_nH_{2n}O_2$, wherein n is and integer of from about 4 to about 10;

electron deficient vinyl ethers of the formula $C_nF_{2n+1}XCl_xO$ and $R_fC_2F_2O$, wherein n is an integer from 0 to 8 and $R_f$ is a $C_nF_{2n+1}$ or halogen radical including Cl, F, Br, I; such as, $CF_3CF=CFO$, $CF_2=CFO$, $CFCl=CFO$;

linear or branched heteroallyls of the formula $C_nH_{2n-1}X$, and linear or branched di-halo heteroallyls of the formula $C_nH_{2n}X_2$, wherein n is an integer from 3 to 8 and X is a halogen radical, Cl, F, Br, I; as well as functionalized allyl alcohols, propargyl alcohols, hydroxyvinyl ether, hydroxybutyl ether, hydroxyethylacrylate, hydroxyethylmethacrylate, 2-hydroxypropylacrylate, 2-hydroxypropylmethacrylate, 4-hydroxybutylacrylate, 4-hydroxybutylmethacrylate, $HOCH_2CH_2O(—CH_2CH_2O—)_xCOR=CH_2$, $HOCH(CH_3)CH_2O(—CH(CH_3)CH_2O—)_xCOR=CH_2$, $HOCH_2CH_2CH_2CH_2O(—CH_2CH_2CH_2CH_2O—)_xCOR=CH_2$, glycerin acrylate, glycerin methacrylate, glycerin diacrylate, glycerin dimethacrylate, pentaerythritol acrylate, pentaerythritol diacrylate, pentaerythritol triacrylate, pentaerythritol methacrylate, pentaerythritol dimethacrylate, pentaerythritol trimethacrylate, methyl 2-hydroxymethyl methyl acrylate, $CH_3OC(O)(HOCH_2)C=CH_2$, N-(hydroxymethyl)acrylamide, N-(hydroxymethyl)methacrylamide, N-[tris(hydroxymethyl)methyl]acrylamide, glycolic acid, $HOCH_2COOH$, lactic acid, $CH_3CHOHCOOH$, 2-hydroxybutyric acid, 3-hydroxybutyric acid, 2-hydroxyisobutryic acid, 4-hydroxybutyric acid lactone, 2-hydroxyethylacetate, ethylene glycol mono-acetate, 2-hydroxy-3-phenoxypropyl acrylate, glyceric acid, $HOCH_2CHOHCOOH$, malic acid, tartaric acid, citric acid, gluconic acid, and its salts Na, K, Ca, Mg, Fe, Cu, $HOCH_2(HCOH)_4CO_2H$, glucaric acid potassium salt, saccharic acid, $HO_2C(CHOH)_4CO_2K$, 2-hydroxyacetamide, 2-hydroxy acetophenone, 3-hydroxy acetophenone, 4-hydroxy acetophenone, 2-hydroxy benzoic acid, 3-hydroxy benzoic acid, 4-hydroxy benzoic acid, 4-hydroxyphenylacetic acid, 2-hydroxycinnamic acid, 3-hydroxycinnamic acid, 4-hydroxycinnamic acid, 3-hydroxy-4-methyoxycinnamic acid, trans-3-hydroxy-4-methyoxycinnamic acid, 4-(2-hydroxyethyl)morpholine, 2-hydroxyethyl sulfone, hydroxymethanesulfinic acid, $HOCH_2SO_2Na$, 4-hydroxybenzenesulfonic acid, and salts, 4-hydroxybenzophenone, 2-hydroxy benzyl alcohol, 3-hydroxy benzyl alcohol, 4-hydroxy benzyl alcohol, 2-hydroxymethyl-12-crown-4,2-hydroxymethyl-15-crown-5,2-hydroxymethyl-18-crown-6, gallic acid, 3,4,5, trihydroxybenzoic acid, 2,4,6 trihydroxybenzoic acid, 2-hydroxyethyl 2-pyrrolidinone, 2,2-hydroxyethyl pyridine, 4,2-hydroxyethylmorpholine, 1,8 dihydroxyanthraquinone, 2,4 dihydroxybenzaldehyde, 3,4 dihydroxybenzaldehyde, 2,4 dihydroxybenzoic acid, 2,5 dihydroxybenzoic acid, 2,6 dihydroxybenzoic acid, 3,4 dihydroxybenzoic acid, 3,5 dihydroxybenzoic acid, 3,4 dihydroxy-1 butene, 2,6 dihydroxy-2-mercaptopyrimidine, 2-thiobarbituric acid, 4-(2,3-dihydroxypropyl) 2-(methylene-4,4-dimethylpentyl) succinate, 2-hydroxy-4-methoxybenzoic acid, 3-hydroxy-4-methoxybenzoic acid, 4-hydroxy-3-methoxybenzoic acid, 3-hydroxy-4-methoxybenzyl alcohol, 4-(hydroxymethyl) phenylboronic acid, 3-(hydroxymethyl)phenylboronic acid, 4-hydroxy-1-naphthalenesulfonic acid, and salts, 4-hydroxy-2,7-naphthalenedisulfonic acid and salts, 2-hydroxy-1-napthoic acid, 3-hydroxy-2-napthoic acid, 6-hydroxynicotinic acid, 4-hydroxy-3-nitrobenzensulfonic acid, 2-hydroxy-5-nitrobenzoic acid, 3-hydroxy-4-nitrobenzoic acid, 2-hydroxy-3-nitropyridine, 2-hydroxy-3-nitropyridine, 4-hydroxy-3-phenylglycine free amine group may be reacted with acrylic acid or methacrylate, 1-(3-hydroxyphenyl)urea, trans-4-hydroxy-1-proline, 1,3,4,5-tetrahydroxycyclohexanecarboxylic acid, methyl glucose, methyl β-D-galactoside, methyl D-maltoside, methyl β-D-mannoside, methyl β-D-xyloside, methyl D-maltoside, methyl β-D-lactoside, ethyl glucoside, ethyl galactoside, ethyl mannoside, ethyl xyloside, propyl glucoside, isopropyl glucoside, butyl glucoside, butyl galactoside, butyl mannoside, $CF_3CHFCF_2CH_2OH$, and $HCF_2CF_2CH_2OH$, as well as, any of the compounds listed hereinabove wherein one or more of the hydroxyl groups is replaced with a $—O—CR^2R^3—CF_2CHFCF_3$ group.

Methods of Making Compounds

Although applicants do not wish to be bound by or to any particular theory of operation, applicants believe one possible mechanism for the formation of certain compounds of the present invention is shown in Reaction Scheme I.

Reaction Scheme I

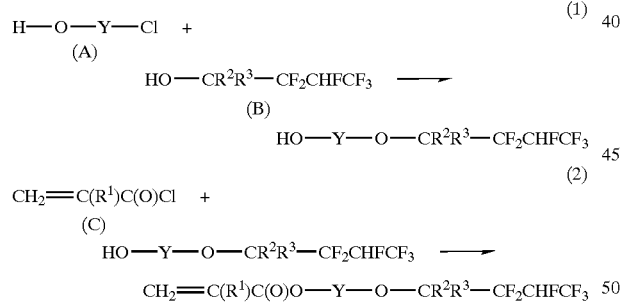

It should be appreciated that any —Cl groups present on the Y groups of compound A can also be converted to $—O—CR^2R^3—CF_2CHFCF_3$ groups via the reaction step 1 shown in scheme I.

Any of a wide range of Compounds A and B can be used in the preparation of the compounds of the present invention. Examples of Compounds A include $HOCH(CH_2Cl)_2$, and the like, and examples of Compounds B include $HO—CH_2—CF_2CHFCF_3$, $HO—CH(CH_3)—CF_2CHFCF_3$, and the like. A variety of such compounds are available commercially or are obtainable by art-recognized procedures. For example, compounds having the structure of Compound B can be made conventionally using the chemistry disclosed in EP 967,193 A2, which is incorporated herein by reference.

Any of a wide range of Compounds C can be used in the preparation of the compounds of the present invention. Examples of such compounds include the acid chloride derivatives of 2-hydroxyethyl methacrylate, 4-hydroxybutyl acrylate, 2-hydroxyethyl acrylate and the like. A variety of such compounds are available commercially or are obtainable by art-recognized procedures.

Those skilled in the art will appreciate that the amounts of Compounds A-C to be used according to the present invention will depend on many variables, including the particular reagents being used and the desired yield from the reaction. The amount of reagents used is preferably an amount effective to achieve about 30% or better, more preferably about 50% or better, even more preferably about 80% or better, and even more preferably about 90% or better, of conversion of the Compound A starting material to desired Compound C product.

Generally, for reaction step 1, the ratio of —Cl moieties of Compound A to be converted to $—O—CR^2R^3—CF_2CHFCF_3$ groups to Compound B may vary from about 2:1 to about 1:2. Preferably, the ratio of —Cl moieties to Compound B is from about 1.5:1 to about 1:1.5, and even more preferably from about 1:1.05 to about 1:1.4.

In certain embodiments, the reaction step 1 of scheme I takes place in the presence of a base. Any of a wide range of bases can be used in the reaction according to the present invention. Examples of suitable bases include organic bases, such as, earth metal hydroxides, including sodium hydroxide and potassium hydroxide, and earth metal carbonates, such as, potassium carbonate and sodium carbonate, and the like. Examples of preferred bases include sodium hydroxide and potassium hydroxide.

Those skilled in the art will appreciate that the conditions under which the reaction step 1 occurs, including the temperature, pressure and period of reaction, will depend on numerous factors, including the particular starting reagents used and the desired reaction yield. In view of the teachings contained herein, those skilled in the art will be able to select the appropriate reaction conditions to achieve the particular desired result. In certain preferred embodiments, the reaction is conducted at a temperature in the range of from about −20 to about 150° C., more preferably in the range of about 25 to about 140° C., and even more preferably about 50 to about 140° C.

The compounds obtained from the aforementioned reaction may be purified by conventional methods known to those skilled in the art. For example, aqueous washes, drying, concentrating under reduced pressure, distillation, HPLC separation, and the like may be used.

In certain embodiments, the reaction step 2 of Scheme I takes place in the presence of a base. Any of a wide range of bases can be used in the reaction according to the present invention. Examples of suitable bases include organic bases, such as, ammonia, secondary amines, tertiary amines including triethylamine, dimethylaniline, pyridine and the like, as well as, inorganic bases, such as, earth metal hydroxides, including sodium hydroxide and potassium hydroxide, and earth metal carbonates, such as, potassium carbonate and sodium carbonate, and the like. Certain preferred bases include those having a pKa value of about 9 to about 11. Examples of preferred bases include triethylamine, potassium carbonate and sodium carbonate.

Any suitable amount of base may be used in the reaction step 2 of the present invention. The amount of base used should be at least sufficient to provide a catalytic amount. Larger amounts of base may be used to partially or completely bind the hydrogen fluoride and/or hydrogen chloride by-products formed by the reaction. Excesses of base, for example, up to about 5 equivalents, may be used. The product distribution may be altered as a factor of the amount of based used. In light of the disclosure herein, those of skill in the art will be readily able to determine the amount of base for use in a given application, without undue experimentation.

In certain preferred embodiments, the reaction step 2 is conducted in a solvent. Suitable solvents include substantially anhydrous, aprotic solvents, such as, methylene chloride, chloroform, carbon tetrachloride, dichloroethane, trichloroethane, tetra-chloroethane, benzene, toluene, chlorobenzene, dimethylformamide, tetramethylene sulphone, dimethyl sulfoxide, acetonitrile, glyme, diglyme, tetrahydrofuran, and the like. Preferred solvents include dimethylformamide and acetonitrile.

Those skilled in the art will appreciate that the conditions under which the reaction step 2 occurs, including the temperature, pressure and period of reaction, will depend on numerous factors, including the particular starting reagents used and the desired reaction yield. In view of the teachings contained herein, those skilled in the art will be able to select the appropriate reaction conditions to achieve the particular desired result. In certain preferred embodiments, the reaction is conducted at a temperature in the range of from about −20 to about 50° C., more preferably in the range of about −10 to about 25° C., and even more preferably about −5 to about 10° C.

Polymers and Polymerization

The present invention further provides polymers comprising a repeating unit derived from a compound of the present invention, or a mixture of two or more compounds of the present invention.

In certain embodiments, the polymers of the present invention comprise homopolymers, comprising repeating units all derived from the same compound of the present invention. In certain other embodiments, the repeating units of the present polymer are derived from a plurality of compounds of the instant invention. Such compositions may be copolymers, block copolymers, terpolymers, polymers comprising four or more different classes of repeating units, combinations of two or more thereof, and the like.

In yet other embodiments, the polymer of the present invention may include one or more repeating units derived from other monomers, oligomers, or polymer compounds that have been copolymerized with at least one compound of the present invention. Suitable other monomers, oligomers, and polymer compounds include, for example, hydrophobic monomers, including, esters of acrylic or methacrylic acid, and longer chain alkyl, dialkyl and aryl acrylamides, where the alkyl or aryl groups include the following: methyl, ethyl, propyl, isopropyl, butyl, isobutyl, amyl, hexyl, phenol and substituted phenols, e.g. 2,6 dimethyl-phenol, benzyl and substituted benzyl materials, octyl, iso-octyl, ethyl hexyl, nonyl, decyl, undecyl, dodecyl, lauryl, stearyl, cyclopentyl, cyclohexyl, and other vinyl compounds, for example, styrene, a-methyl styrene, vinyl acetate, vinyl propionate, acrylonitrile, vinyl chloride, vinyl fluoride, vinylidene chloride, vinylidene fluoride, butadiene, isopreneydrophilic, and the like, as well as, hydrophilic monomers, for example, hydrophilic olefins and simple/short chain acrylamides, 2 hydroxyethyl acrylate/methacrylate, 2-hydroxypropyl acrylate/methacrylate, 2-dimethylamino-, 2-diethyl amino-, 3-dimethyl aminopropyl-, 3-diethylaminopropyl-, polyethyleglycol mono acrylate or methylate, these can be long chain, MW 2000, acrylamide, methylolacrylamide, methacrylamide, dimethylacrylamide, dimethylmethacrylamide, acrylic acid, methacrylic acid, n-vinylpyrrolidone, 2 and 4 vinyl pyridine, vinyl carbazole, AMPS: 2-acrylamido-2-methylpropane sulfonic acid, allyl alcohol, propargyl alcohol, hydroxyethylvinyl ether, hydroxybutyl vinyl ether, hydroxycyclohexyl-vinyl ether, and the like. Other suitable co-monomers include cross-linking monomers, for example, ethylene glycol diacrylate/methacrylate, diethylene glycol, triethyleneglycol, vinyl acrylate or methacrylate, allylacrylate or methacrylate, divinyl benzene, trimethylol propane triacrylate or methacrylate, pentaerythritol triacrylate or methacrylate, pentaerythritol diacrylate or methacrylate, glycidyl acrylate or methacrylate, various glycol di-acrylates and methacrylates, 2-chloro ethyl acrylate, and the like, as well as fluorinated monomers, for example, 2-hexafluoropropyl allyl ether, 1,1,2,2, tetrafluoroallyl ether, 2,2,2 trifluoroethyl trifluorovinyl ether, 2,2,2 trifluoroethyl vinyl ether, trifluoromethyl trifluorovinylether, 2,2,2 trifluoroethyl methacrylate, 2,2,3,4,4,4-hexafluorobutylmethacrylate trimethylol propane, and the like.

By copolymerizing the present compounds with other monomers, oligomers, and polymers, the water-repellency, oil-repellency and stainproofing properties, as well as various characteristics, e.g. cleaning resistance, washing resistance and wear resistance, solubility in solvent, hardness and feeling, and application as a photoresist, can be improved according to necessity. Any suitable relative amounts of the present compounds and other compounds can be used according to the present invention. For example, certain polymers preferred for use in treating textiles to improve the water-repellency thereof include those derived from: $CH_2=CHCONH(CH_2OHFP)_3$, methyl acrylate, and 2-hydroxyethyl acrylate in a mol ratio of about 100:10–40:1–20, respectively; $CH_2=C(CH_3)CONH(CH_2OHFP)_3$ and $CH_2=CHC(O)OCH_2CF_3$ in a mole ratio of from 1:1 to 10:1; $CH_2=CHCONH(CH_2OHFP)_3$ $CH_2=CHC(O)OCH_2CF_3$, and 2-hydroxyethyl acrylate in a mole ratio of from 100:1–40:1–10; and $CH_2=CHCONH(CH_2OHFP)_3$, methyl methacrylate, and acrylic acid in a mole ratio of 100:10–50:1–10. In certain preferred embodiments, the amount of other polymers used in the present invention is from about 30–90% by weight of the polymer of the present invention. In light of the disclosure herein, those of skill in the art will be readily able to produce polymers of the present invention having physical and chemical properties suitable for a given application, without undue experimentation.

The polymers of the present invention are prepared by polymerizing one or more of the present compounds, optionally in the presence of any additional monomer, oligomer, or polymer compounds to be copolymerized therewith. Any of a wide range of known methods for polymerizing the present compounds can be used according to the present invention. Examples of suitable polymerization methods include bulk polymerization, solution polymerization, emulsion polymerization where the monomers can undergo free radical polymerization, ionic polymerization (cationic and anionic with suitable catalysts), e-beam induced polymerization, addition polymerization such as Diels-Alder coupling and condensation reactions. In certain preferred embodiments, the polymers of the present invention are produced via bulk or solution polymerization. In a particularly preferred embodiment, the present polymers are produced via solution polymerization.

Any of the polymerization methods according to the present invention may comprise reacting one or more compounds of the present invention in the presence of a polymerization initiator and/or a surfactant. Any of a wide range of conventional initiators and surfactants may be used according to the present invention. Suitable surfactants include, anionic surfactants, for example, salts of carboxylic, phosphoric, and sulfonic acids, such as, sodium lauryl sulfate and sodium dioctyl sulfosuccinate, as well as, cationic surfactants, for example, ammonium salts, such as, cetyl trimethylammonium bromide, and, non-ionic surfactants including Tween® polyoxyethylene sorbitan esters, sorbitan esters, and Brij® polyoxyethylene ethers, and the like.

In light of the disclosure herein, those of skill in the art will be readily able to optimize radical initiators, optionally solvents, amounts thereof, and reaction conditions for preparing the present polymers, without undue experimentation. In certain preferred embodiments, the polymerization is conducted at a temperature in the range of about 25° C. to about 100° C., using about 1 mole percent of initiator relative to the amount of compound or compounds of the present invention.

Uses of the Polymers

The polymers of the present invention have utility in a wide range of applications. For example, the present polymers can be used in compositions for treating a wide variety of substrates, such as fibers, carpets, fabrics, textiles, paper, and the like, to impart thereto a variety of desirable properties including increased water and oil repellency, as well as increased soil and stain resistance. The compositions of the present invention may also be added to paint to serve as an anti-graffiti additive.

Accordingly, the present invention provides a composition comprising at least one polymer according to the present invention. The present compositions may comprise one or more polymers according to the present invention and may further comprise one or more optional other polymeric materials. Examples of suitable other polymeric materials for use in the compositions of the present invention include homopolymers or copolymers of the following: acrylates, such as, methyl methacrylate and ethyl methacrylate, urethanes, butyrals, styrenic copolymers, polyvinylacetates, and the like. In certain embodiments, preferred other polymeric materials comprise copolymers of methyl methacrylate and ethyl methacrylate (available commercially in the form of an extender emulsion). The other polymeric materials of the present invention may be blended, reacted, or cross-linked with the polymers of the present inventions to provide compositions having any of a wide range of desired properties.

In certain embodiments, the compositions of the present invention are emulsions, and preferably, aqueous emulsions. Accordingly, in preferred embodiments, the present compositions comprise water as a solvent. Any suitable amount of water may be used in the present compositions, and in light of the disclosure herein, those of skill in the art will be readily able to select an appropriate amount of water for a given application.

The preferred aqueous compositions of the present invention may further comprise an organic co-solvent. Preferred organic co-solvents are those that tend to be water-miscible and have low toxicity. Examples of preferred other organic solvents include alcohols, ketones, ethers, such as, diethylene glycol diethylether, diethylene glycol dimethylether, propylene glycol dimethylether, water-miscible glycol ether, e.g. propylene glycol monomethylether, propylene glycol mono ethylether, propylene glycolmonopropylether, propylene glycol monobutylether, ethylene glycol monobutylether, dipropylene glycol monomethylether, diethyleneglycol monobutylether; lower esters of monoalkylethers of ethyleneglycol or propylene glycol, such as, propylene glycol monomethyl ether acetate, and mixtures of two or more thereof. Any suitable amount of other organic solvents may be used. Preferably, the amount of organic co-solvent used is less than 10% by weight based on the total weight of the composition.

The compositions of the present invention may also comprise other additives including leveling aids, such as, butyl carbitol, trimethylpentane diol monoisobutyrate, and the like, film-forming polymers and monomers, such as, poly(vinyl alcohol), diethylene glycol methyl ether methacrylate, diethylene glycol 2-ethylhexyl acrylate, poly (ethylene glycol) methyl ether methacrylate, and the like, as well as other additive used conventionally in compositions for the treatment of textile and paper-type substrates.

Any suitable amounts of the present polymers and additives may be used in the compositions of the present invention. In certain embodiments, the compositions comprise from about 0.1 to about 50 percent, by weight of the entire composition, of a polymer according to the present invention. In certain preferred embodiments, from about 2 to about 50 weight percent of polymer of the present invention.

In certain embodiments, the compositions of the present invention are used in methods for treating a substrate comprising applying a composition of the present invention onto a substrate and drying/curing said composition on said substrate.

Any of a wide range of methods for applying the present composition onto a substrate may be used according to the present invention. Suitable methods include, for example, padding, foaming, spraying and the like.

In certain preferred embodiments, the composition is dried or cured by exposing the composition to heat. As will be readily appreciated, the composition may be cured using any suitable heat source. While the preferred embodiment involves heat-curing the curable composition, one skilled in the art will appreciate that many variations of the method within the scope of the claims is possible depending on the nature of the curable composition. For example, if desired, the curing of the curable composition may be accelerated using microwave treatment procedures known in the art.

The present invention also provides for a coating or film formed by curing a curable composition of the present invention.

EXAMPLES

As used in the following examples, the abbreviation "HFP" refers to both the saturated and unsaturated groups derived from hexfluoropropene, i.e., —$CF_2CHFCF_3$ and —$CF=CFCF_3$.

Example 1

This example illustrates the emulsion polymerization of $CF_3CHFCF_2CH_2OC(O)CH=CH_2$.

The acrylate of 2,2,3,4,4,4-hexafluorobutanol was obtained from the Aldrich Chemical Company. The acrylate (9.9 g), 0.10 g sodium persulfate, 0.40 g sodium dodecyl sulfate, and 30 mL water were combined and purged with nitrogen to remove oxygen from the system. The mixture was then heated to 50° C. with good stirring in a nitrogen atmosphere for 6 hours. A homopolymer latex was obtained.

Example 2

This example illustrates the preparation of a copolymer of $CF_3CHFCF_2CH_2OC(O)CH=CH_2$ and $CH_2=CHCONHC(CH_2OHFP)_3$ In a manner similar to Example 1, a copolymer latex was prepared from 5.0 g $CF_3CHFCF_2CH_2OC(O)CH=CH_2$, 5.0 g $CH_2=CHCONHC(CH_2OHFP)_3$ (Compound B), 0.13 g sodium persulfate, 0.64 g sodium dodecyl sulfate, 0.26 g butyl carbitol ($CH_3(CH_2)_3O(CH_2CH_2O)_2H$, a leveling agent), and 72.5 mL water (reaction time 20 h at 50° C.).

Example 3

This example illustrates the preparation of poly $[CH_2=CHCO_2CH(CH_2OCH_2CF_2CFHCF_3)_2]$.

The compound $CF_3CFHCF_2CH_2OH$ (50.0 g, 0.275 mol), $HOCH(CH_2Cl)_2$ (17.7 g, 0.137 mol), $C_{16}H_{33}NMe_3$ Br (2.0 g), NaOH (11.0 g, 0.275 mol) and water (14 mL) were stirred at 120–130° C. for 15 h. Water (100 mL) was added and the mixture extracted with twice with 40 mL $CH_2Cl_2$. The extract was dried with $Na_2SO_4$. After removing solvent, the residue was fractionally distilled at 6–7 torr. Twenty-two grams of colorless liquid was collected, bp 85–90° C. (HPLC purity 94%). $^1H$ NMR for $H^aOCH^b(CH_2^cOCH_2^d CF_2^eCF^fH^gCF_3^h)_2$: δ3.70 ($H^a$, d,1H); 3.95 ($H^b$, m, 1H); 3.65 ($H^c$, m, 2H); 3.80 ($H^d$, m 2H); 5.00 ($H^g$, m, 1H) ppm. $^{19}F$ NMR: −72.5 ($F^h$, 3F); −119 ($F^e$, AB system, 2F); −214 ($F^f$, 1F) ppm.

An addition funnel was charged with $CH_2=CHCOCl$ (2.0 g) and $CH_3CN$ (10 mL). This solution was added to a mixture of the alcohol obtained above (HOCH $(CH_2OCH_2CF_2CFHCF_3)_2$, 6.7 g, 0.016 mol), $Et_3N$ (3.0 g) and $CH_3CN$ (30 mL) that was cooled to 0° C. The acryloyl chloride solution was added in about 30 min. After stirring for 4 h, the reaction mixture was filtered and solvent removed under reduced pressure. The residue was dissolved in 50 mL $CH_2Cl_2$, washed with water, and dried ($Na_2SO_4$). Distillation at 5–7 torr gave 6.2 g of $CH_2=CHCO_2CH(CH_2OCH_2CF_2CFHCF_3)_2$, bp 90–100° C. $^{19}F$ NMR indicated that approximately 6% of the product contained a $CH_2CF=CFCF_3$ group. $CH_2=CHCO_2CH(CH_2OCH_2CF_2CFHCF_3)_2$ (6.0 g), AIBN (0.060 g), heptane (20 mL) and ethyl acetate (20 mL) were combined. The stirred solution was purged with $N_2$ and heated to 50° C. for 20 h. A transparent polymer solution was obtained.

Example 4

This example illustrates the solution polymerization of $CF_3CHFCF_2CH_2OC(O)CH=CH_2$ Hexafluorobutyl acrylate (8.0 g) and 0.80 g AIBN were dissolved in 20 mL each of ethyl acetate and heptane. After purging nitrogen through the solution to remove oxygen, the solution was heated to 50° C. for 15 hours.

Example 5

This example illustrates the low surface energy of polymers of the present invention.

Thin films of polymers on glass slides were prepared by placing a solution of the polymer on the slide. After about 10 seconds, the solution was drained off the slide. The slide was then dried in an oven prior to making contact angle measurements with a goniometer. Oil repellency tests were also performed according to AATCC test method 118-1997. This test measures the rate at which hydrocarbon oils of different molecular weight spread on a filter paper that has been treated with the test polymer. A higher numerical grade indicates more resistance to the spreading of hydrocarbon fluids. The oil used in the contact angle measurements is light mineral oil. The resulting data is shown in Table 1.

TABLE 1

| No. | Monomer(s) (acrylate of) | Contact angle (glycol) | Contact angle (oil) | Repellency grade | Comment |
|---|---|---|---|---|---|
| 1 | $CF_3CH_2OH$ | 70.8 | 53.1 | 1 | comparative emulsion |
| 2 | stearyl alcohol | 81.3 | 49.2 | 1 | comparative; solution |
| 3 | $CF_3CHFCF_2CH_2OH$ | 88.9 | 64.0 | 4.5 | emulsion |
| 4 | $CF_3CHFCF_2CH_2OH$ | 88.5 | 77.7 | 5.0 | solution |
| 5 | $CF_3CHFCF_2CH_2OH$ co-Compound B | 75.2 | 60.2 | 4.5 | emulsion; 1:1 by weight |
| 6 | Compound A | 77.8 | 57.0 | 3.0 | solution |
| 7 | $CF_3CHFCF_2CH_2OH$ co-Compound C | * | * | 2.5 | solution 1:1 mole ratio |
| 8 | $CF_3CHFCF_2CH_2OH$ co-Compound C | 68.0 | 62.5 | 3.0 | emulsion 2.5:1 mole ratio |
| 9 | $CF_3CHFCF_2CH_2OH$ co-Compound C | 86.7 | 64.1 | 2.0 | emulsion 5:1 mole ratio |
| 10 | $CF_3CHFCF_2CH_2OH$ co-Compound D | * | * | 2.5 | solution 1:1 mole ratio |

Compound A is the acrylate of $(CF_3CHFCF_2CH_2OCH_2)_2CHOH$;
Compound B is $CH_2=CHCONHC(CH_2OHFP)_3$;
Compound C is $CH_2=CHC(O)OCH_2CH_2OH$ (not its acrylate);
*tacky film, contact angles unstable;
Compound D is a mixture of $CH_2=CHC(O)OCH_2CH_2OC_6F_{11}$ and $CH_2=CHC(O)OCH_2CH_2OC_6HF_{12}$

What is claimed is:

1. A compound described by the following formula:

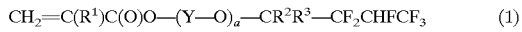     (1)

wherein: $R^1$, $R^2$ and $R^3$ are independently hydrogen or lower alkyl, Y is a divalent aromatic moiety derived from a monovalent moiety selected from the group consisting of unsubstituted aryls and substituted aryls, or a divalent aliphatic moiety selected from the group consisting of $-CH(CH_3)CH_2-$, $-CH(CH_2OCR^2R^3-CF_2CHFCF_3)CH_2-$, and $-C(CH_3)_2CH_2-$, and a is one.

2. The compound according to claim 1 wherein Y is selected from the group consisting of $-CH(CH_3)CH_2-$, $-CH(CH_2OCR^2R^3CF_2CHFCF_3)CH_2-$, and $-C(CH_3)_2CH_2-$.

3. The compound of claim 2 described by the following formula:

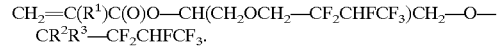

* * * * *